(12) United States Patent
Dohrup et al.

(10) Patent No.: US 10,087,578 B2
(45) Date of Patent: Oct. 2, 2018

(54) DEVICE FOR DISCHARGING PRETREATED BIOMASS FROM HIGHER TO LOWER PRESSURE REGIONS

(71) Applicant: Inbicon A/S, Fredericia (DK)

(72) Inventors: Jesper Dohrup, Holbaek (DK); Brian Eskesen, Brenderup Fyn (DK); Kit Kellebjerg Mogensen, Fredericia (DK)

(73) Assignee: INBICON A/S, Fredericia (DK)

( * ) Notice: Subject to any disclaimer, the term of this patent is extended or adjusted under 35 U.S.C. 154(b) by 129 days.

(21) Appl. No.: 14/910,531

(22) PCT Filed: Aug. 11, 2014

(86) PCT No.: PCT/DK2014/050240
§ 371 (c)(1),
(2) Date: Feb. 5, 2016

(87) PCT Pub. No.: WO2015/018423
PCT Pub. Date: Feb. 12, 2015

(65) Prior Publication Data
US 2016/0215448 A1  Jul. 28, 2016

Related U.S. Application Data

(60) Provisional application No. 61/863,931, filed on Aug. 9, 2013.

(30) Foreign Application Priority Data

Aug. 9, 2013  (DK) ................... 2013 70441

(51) Int. Cl.
*B01J 3/02*   (2006.01)
*D21C 1/10*   (2006.01)
(Continued)

(52) U.S. Cl.
CPC ............... *D21C 1/10* (2013.01); *B01J 3/002* (2013.01); *B01J 3/008* (2013.01); *B01J 3/02* (2013.01);
(Continued)

(58) Field of Classification Search
CPC .. C10L 5/44; C10L 9/086; D21C 1/02; D21C 1/10; B01J 3/002; B01J 3/00; B01J 3/008;
(Continued)

(56) References Cited

U.S. PATENT DOCUMENTS 2,474,862 A   7/1949  Richter
2,858,213 A   10/1958 Durant et al.
(Continued)

FOREIGN PATENT DOCUMENTS

AU   2011 292 083 A1   2/2013
CN      101827645 A    9/2010
(Continued)

*Primary Examiner* — Mark Halpern
(74) *Attorney, Agent, or Firm* — Womble Bond Dickinson (US) LLP

(57) ABSTRACT

Provided is a discharge device for discharging pretreated biomass from a pressurized reactor. The device comprises:
 a vessel having an opening to a high pressure region at the top, and configured to be connected with a pressurized biomass pretreatment device;
 one or more inlet openings situated along the sides of the vessels through which water or liquid may be added;
 an orifice or valve at a lower part of said vessel, said orifice or valve being configured to eject pretreated biomass, optionally into a pipeline.
The discharge device is characterised in that it comprises mechanical agitation means, said agitation means comprising an agitation element arranged in the interior of said vessel at a lower part of said vessel, and being configured to provide agitation of the content of said vessel, wherein said agitation means being adapted to withstand a pressure in the interior of a said vessel of 10 bar or more. The agitation means provides for a temperature equalization within a specific vertical range of heights of an aqueous slurry present in said vessel, thereby eliminating disadvantages of the prior art devices and methods.

25 Claims, 7 Drawing Sheets

(51) Int. Cl.
*C10L 5/44* (2006.01)
*C10L 9/08* (2006.01)
*B01J 3/00* (2006.01)
*B01J 3/04* (2006.01)
*D21C 1/02* (2006.01)

(52) U.S. Cl.
CPC . *B01J 3/04* (2013.01); *C10L 5/44* (2013.01); *C10L 9/086* (2013.01); *D21C 1/02* (2013.01); *B01J 2219/0018* (2013.01); *B01J 2219/00058* (2013.01); *B01J 2219/00065* (2013.01); *B01J 2219/00067* (2013.01); *B01J 2219/00162* (2013.01); *B01J 2219/00177* (2013.01); *B01J 2219/00182* (2013.01); *B01J 2219/00189* (2013.01); *C12P 2201/00* (2013.01); *Y02E 50/10* (2013.01); *Y02E 50/30* (2013.01)

(58) Field of Classification Search
CPC ...... B01J 2219/0018; B01J 2219/00177; B01J 2219/00189
USPC .......................................................... 162/17
See application file for complete search history.

(56) References Cited

U.S. PATENT DOCUMENTS

| 3,035,962 A | 5/1962 | Schinn |
| 5,277,491 A | 9/1994 | Burnett et al. |
| 2012/0227822 A1 | 9/2012 | Humphreys |

FOREIGN PATENT DOCUMENTS

| CN | 102057051 A | 5/2011 |
| DE | 941 529 | 12/1956 |
| DE | 10 2011 001108 A1 | 9/2012 |
| EP | 1 726 356 A1 | 11/2006 |
| WO | WO 2009/015409 A1 | 2/2009 |
| WO | WO 2009/125292 A2 | 10/2009 |
| WO | WO 2009/147512 A2 | 12/2009 |
| WO | WO 2011/084761 A2 | 7/2011 |
| WO | WO 2012/024314 A1 | 2/2012 |
| WO | WO 2012/128901 A1 | 9/2012 |

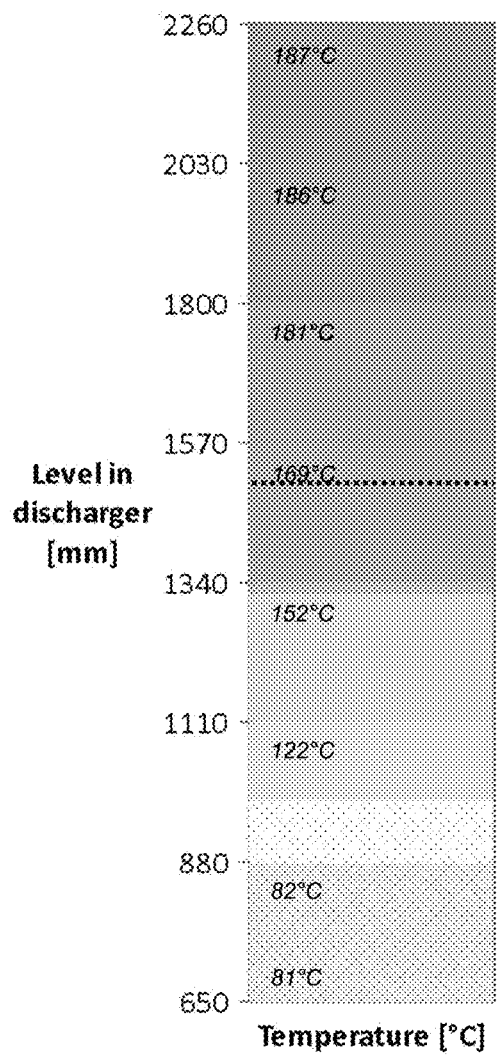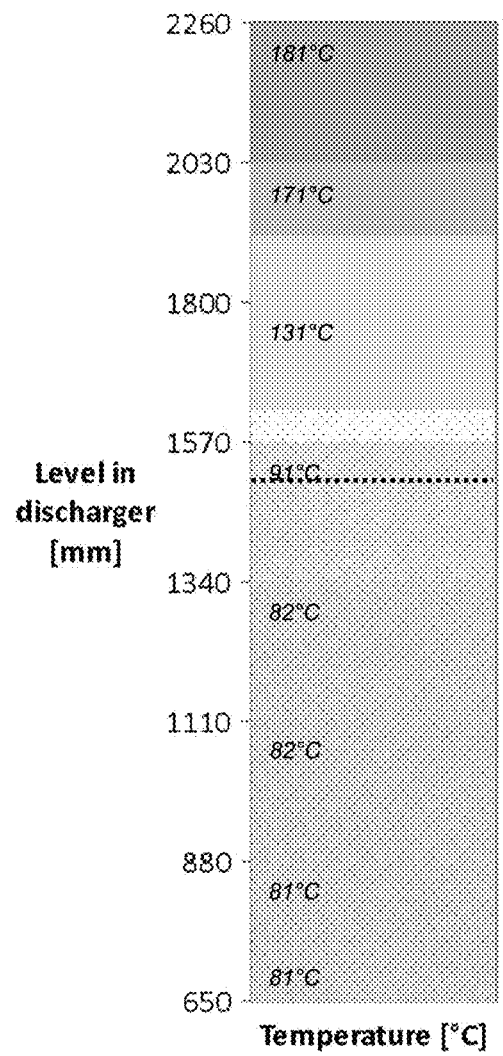
Fig. 5a
Fig. 5b

DEVICE FOR DISCHARGING PRETREATED BIOMASS FROM HIGHER TO LOWER PRESSURE REGIONS

CROSS-REFERENCE TO RELATED APPLICATIONS

This application is a national stage filing under 35 U.S.C. 371 of PCT/DK2014/050240, filed Aug. 11, 2014, which International Application was published by the International Bureau in English on Feb. 12, 2015, and application claims priority from Denmark Application No. PA 2013 70441, filed Aug. 9, 2013, and U.S. Provisional Application No. 61/863,931, filed Aug. 9, 2013.

FIELD OF THE INVENTION

The present invention relates to a discharge device and a method for discharging biomass, that has been subject to pressurized treatments, into lower or atmospheric pressure regions. Moreover, the present invention relates to an apparatus comprising such discharge device in combination with a pretreatment reactor. Furthermore, the present invention relates to use of such a discharge device for transferring pretreated biomass from higher to lower pressures.

BACKGROUND OF THE INVENTION

An intense interest has arisen in fermentation and gasification of carbohydrate-rich biomass to provide alternatives to petrochemical sources for fuels, livestock feeds and for organic chemical precursors.

Lignocellulosic biomasses including industrial and agricultural wastes have proved particularly interesting as carbohydrate sources.

For lignocellulosic biomasses subject to processing by enzymatic hydrolysis, pretreatment is generally required in order to separate lignin and hemicellulose from cellulose fibers and thereby increase catalytically effective access of hydrolytic enzymes. A variety of pretreatment processes have been reported, many of which rely on high temperature treatments at high pressures. For review, see ref. 1 and 2.

Discharge of pretreated biomasses from high pressure regions to subsequent processing at lower or atmospheric pressure presents a technical problem that has previously been solved by three general approaches. Sluice systems suitable for semi-continuous processing have been developed that provide pressure sealed transfer of biomass from regions of different pressure. See for example, WO 2011/024145, which is hereby incorporated by reference in entirety.

Alternatively, discharge of pretreated biomass from high pressure regions has been achieved using "steam explosion," where biomass is literally blown out of a pressure treatment device into a blow tank. See for example U.S. Pat. No. 6,506,282. Or alternatively still, biomass can be discharged from pressurized pretreatment reactors by means of a "hydrocyclone" system, such as that described in WO 2009/147512 A2, which is hereby incorporated by reference in entirety.

WO 2009/147512 A2 discloses a device for discharging pretreated biomass from higher to lower pressure regions. Pretreated, hot biomass is added under high pressure at the top of a discharge vessel, which is partially filled with water or aqueous solution. The vessel comprises a plurality of water jets situated on its sides through which water or aqueous solution is injected in order to establish a strong turbulence in the lower part of the vessel.

This turbulence, preferably a vortex turbulence or "hydrocyclone", blends biomass and water prior to its ejection at high speed as a slurry through an orifice or valve at the bottom of the vessel. A stable temperature stratification is established within the discharge vessel, whereby hot water remains at the top of the vessel, reducing heat and steam loss from the pretreatment reactor.

Within the pulp and paper industry it is well known to use a pulper for disintegration of waste paper fibres. Such a pulper comprises a vessel comprising in a lower part a rotator or agitator in the form of a conical screw which imparts physical impact to the waste paper thereby resulting in a disintegration of the waste paper fibres. During use of such a paper pulper process water is added to the waste paper. An example of such a pulper for use in the waste paper industry is disclosed in U.S. Pat. No. 4,460,132. The apparatus disclosed in U.S. Pat. No. 4,460,132 comprises no means for being connected with a pressurized biomass pretreatment device and is therefore not suitable for use for discharging pretreated biomass from higher to lower pressures.

Another apparatus for use in the paper and pulp industry is disclosed in U.S. Pat. No. 4,725,295. U.S. Pat. No. 4,725,295 discloses an apparatus for separating solid particulates from a gaseous fluid in pressurized processing system for use within the paper pulping industry. The apparatus comprises a steaming tube having inlets at its top for wood chips and steam. In the lower part of the steaming tube is arranged a rotary agitator. Also arranged at the lower part of the steaming tube is a discharge for wood chips which have not been made into pulp. Downstream of the steaming tube the manufactured pulp passes a thermo-mechanical refiner, whereafter the pulp, driven by pressure, enters a cyclone. The cyclone itself comprises an upper part comprising a steam exhaust outlet and a lower part comprising an impeller. The impeller is designed for sweeping out paper pulp via a pulp outlet orifice using the sweep orifice principle. As the wood chips in the process is mainly treated with steam with essentially no liquid water being present, the problems of depressurizing an aqueous slurry of a biomass comprising considerably amounts of liquid water being present at super atmospheric pressures are not encountered in the invention of U.S. Pat. No. 4,725,295. The apparatus disclosed in U.S. Pat. No. 4,725,295 does not provide any means allowing safe transfer of an aqueous slurry of a biomass comprising considerably amounts of liquid water being present at super atmospheric pressures from this super atmospheric region to a low pressure region.

Other systems involving combinations of agitators in the processing of slurries or fluids are disclosed in WO 2009/137867 A1, WO 03/045525 A1 and U.S. Pat. No. 6,428,591 B1, respectively.

WO 2009/137867 A1 discloses an apparatus for deaerating a feed liquid comprising a liquid suspension or pulp. The apparatus comprises a feed conduit to convey a feed liquid into a separator. The separator comprising a mechanical agitator for inducing a rotational flow of the feed liquid in a separation chamber such that the rotational flow generates a centrifugal vortex to separate the feed liquid into a first component consisting essentially of froth or gas and a second component consisting essentially of deaerated liquid or sludge. A lower output channel allows for conducting the second component out of the separator. An overflow channel in the form of an outlet for froth is arranged in an upper part of the separator, hence providing direct access from the interior of the separator to a point outside the separator. Due to the presence of this overflow channel, the separator disclosed in WO2009/137867 A1 will not be suitable for processing sludge being present at superatmospheric pressures.

WO 03/045525 A1 discloses a vortex separator for separating materials into three fractions having different specific gravity. The separator comprises a vortex tube having an upper end and a lower end. The upper end comprises a feed inlet for introducing material into the separator. The lower end of the separator comprises a lowest outlet opening arranged at an inner location of the separator and adapted to collect the materials having the highest specific gravity; a highest outlet opening arranged at an outer location of the separator and adapted to collect the materials having the lowest specific gravity; and a middle outlet opening arranged at a middle location of the separator and adapted to collect the materials having a medium specific gravity. An impeller for creating a vortex of the materials being fed to the separator is arranged at top of the separator. Due to the arrangement of the stirrer at the top, this apparatus will not be suitable for providing stirring of a slurry of a solid material entering the apparatus and specifically this apparatus will not be suitable for transferring pretreated biomass from higher to lower pressure regions.

U.S. Pat. No. 6,428,591 B1 discloses a cyclone for use in a pressurized materials processing system, such as a medium density fiberboard (MDF) processing system, for separating solid material which is entrained in a gaseous fluid maintained at elevated pressure and for reducing the emission of VOCs. The cyclone comprises a housing having an upper end, a lower end and a substantially cylindrical side wall defining a longitudinal axis. An inlet is formed within the housing proximate to the upper end and is tangentially oriented relative to the side wall for inducing the fluid flow to rotate about the longitudinal axis, thereby imparting centrifugal force on the solid material. A gaseous fluid outlet extends upwardly from the upper end of the housing for providing egress of a first, or separated, portion of the gaseous fluid. An outlet for solids is formed within the housing and positioned proximate the lower end. An agitator assembly is positioned within the housing proximate the lower end. The agitator assembly includes a vertically extending, rotatably supported drive shaft coaxially disposed with the longitudinal axis. The agitator assembly furthermore comprises a number of fixed anti-rotation members extending from the inner side of the housing to a central part of the housing. Due to the presence of these fixed anti-rotation members and the viscous nature of aqueous slurries of lignocellulosic biomass, the apparatus disclosed in U.S. Pat. No. 6,428,591 B1 will not be suitable for processing lignocellulosic biomass because of clogging risks.

In production scale processing of lignocellulosic biomass, we have under certain conditions experienced negative complications from use of the hydrocyclone system described in WO 2009/147512 A2.

This hydrocyclone system produces a temperature gradient within the fluid volume contained by the system. Pretreated biomass is released from a pressurized reactor at temperatures in the order of 170 degrees C. or higher into a fluid volume within the hydrocyclone. Water jets infuse hot water into the system so as to break up clumps of pretreated biomass material and provide for a smooth, continuous output of fluidized pretreated biomass slurry. But the result is invariably that a temperature gradient occurs within the hydrocyclone, the water at the top of the vessel, closest to the outlet from a pressurized reactor, being considerably warmer than the water at the outlet from the hydrocyclone.

It has been found that when using a device disclosed in WO 2009/147512 A2 for transferring a discharging hydrothermally pretreated biomass from higher to lower pressure regions, an undesirably high percentage of C5-sugars, such as xylan species, originally present in the lignocellulosic material is inevitably lost into the liquid phase of slurry. Such a loss of C5 sugars accordingly implies a lower yield of ethanol in the case where a hydrothermally pretreated lignocellulosic solid material is intended for hydrolysis and subsequent fermentation into ethanol.

As used herein the term "xylan" is used generically to refer to all oligo and polymer lengths of xylose, which is the predominant C5 sugar originating from hemicellulose. However "xylan" as measured includes a contribution of monomeric soluble xylose such that soluble "xylan" includes "xylose."

Furthermore, with the device disclosed in WO 2009/147512 A2 it has been found that concurrently to this loss of C5-sugars into the liquid phase of the slurry, a furfural built-up in the liquid phase appears. It is well-known that furfural acts as a fermentation inhibitor for certain specific fermentation microorganisms in an ethanol fermentation of C5- and C6 sugars. Even small amounts of furfural present in liquid traces of the fibrous lignocellulosic biomass may represent a considerably inhibiting effect for the sugar fermenting microorgansims.

Moreover, with the device disclosed in WO 2009/147512 A2, under certain conditions, a still layer accumulates on the top of the hydrocyclone, in warmer temperatures, while "clumps" of pretreated biomass sediment to the bottom of the reactor, in cooler temperatures. As a consequence of this inhomogeneous distribution of pretreated biomass within the temperature gradient established within the hydrocyclone, the biomass may experience an inhomogeneous additional "cooking" after the primary pressurized pretreatment is concluded. This in turn causes difficulties in subsequent processing steps. Furthermore, as a consequence of sedimenting clumps of pretreated material accumulating on the bottom and sides of the reactor, a significant incidence of "lignin charring" may occur, which introduces a tendency for "clogging" of filters and pumps used in subsequent processing steps.

Accordingly, there exists a need for improved devices and methods for discharging pretreated biomass from higher to lower pressure in which the above outlined problems are eliminated.

BRIEF DESCRIPTION OF THE INVENTION

This need is fulfilled with the discharge device, the apparatus, the use and the method according to the present invention.

Accordingly, the present invention relates to a discharge device for discharging pretreated biomass from higher to lower pressure, said discharge device in the orientation intended for use comprising:
  a vessel having an opening to a high pressure region at the top, and configured to be connected with a pressurized biomass pretreatment device;
  one or more inlet openings situated along the sides of the vessels through which water or liquid may be added;
  an orifice or valve at a lower part of said vessel, said orifice or valve being configured to eject pretreated biomass, optionally into a pipeline;

characterized in that the discharge device comprises mechanical agitation means, said agitation means comprising an agitation element arranged in the interior of said vessel at a lower part of said vessel, and being configured to provide agitation of the content of said vessel, wherein said agitation means being adapted to withstand a pressure in the interior of a said vessel of 10 bar or more.

The present invention additionally relates to an apparatus comprising a discharge device according to the present invention in combination with a hydrothermal pretreatment reactor;

wherein said hydrothermal pretreatment reactor comprising a cylinder being essentially horizontally arranged and having an inlet for biomass at a first axial end and an outlet for biomass at a second axial end opposite to said first end;

wherein said cylinder comprises in its interior a rotatable auger screw, said auger screw being configured for conveyance of biomass from said first axial end to said second axial end;

wherein said cylinder furthermore comprises one or more inlets for steam and/or water;

wherein said outlet for hydrothermally pretreated biomass at a second axial end of said cylinder being connected to said opening arranged at the top of the vessel of said discharge device.

The present invention also relates to the use of a discharge device according to the present invention or use of an apparatus according to the present invention for transferring a pretreated biomass from higher to lower pressures.

Finally, the present invention relates to a method for discharging biomass from higher to lower pressure, comprising:

i) loading pretreated biomass originating from a higher pressure environment into an upper end of a vessel so as to obtain in said vessel a lower aqueous slurry comprising biomass and an upper gaseous fraction;
ii) performing a mechanical agitation of said aqueous slurry in the lower part of said vessel by means of a mechanical agitation element arranged in the interior of said vessel;
iii) supplying a stream of aqueous liquid into the vessel;
iv) unloading aqueous slurry comprising pretreated biomass from a lower part of said vessel.

In the discharge device and the use thereof and in the method according to the present invention, it has surprisingly been found that a reduction of loss of C5-sugars, such as xylan species, from the fibrous lignocellulosic biomass into the liquid fraction can be considerable reduced, compared to the device and method disclosed in WO2009/147512 A2. Such C5 sugars represent valuable carbon sources for fermentation organisms in a downstream processing of the pretreated lignocellulosic biomass, thus contributing to increased yield of the target substances.

Furthermore, it has surprisingly been found that in the discharge device, in the apparatus and in the use thereof and in the method according to the present invention it is possible to reduce the concentration of furfural in the liquid fraction accompanying the fibrous lignocellulosic fraction, compared to the results obtained with the device and method described in WO2009/147512 A2.

Accordingly, the significantly reduced concentration of furfural in the liquid traces of the fibrous lignocellulosic biomass implies a highly beneficial effect in terms of improved yields of target fermentation substances in downstream further processing of the biomass.

In the event that the lignocellulosic biomass has been pretreated at a temperature which will result in melting part of or all the lignin of the lignocellulosic biomass, the device and method described in WO2009/147512 A2 may not be capable of handling lignin lumps comprising agglomerates of lignin particles adhering to each other. These lumps may clog the exits port of the device disclosed in WO2009/147512 A2 thus necessitating a stop, a dismantling and cleaning of the device.

By including a mechanical agitation means as in the present invention, the problems associated with such clogging are eliminated because the mechanical agitation means will upon impact with such lumps comminute these lumps to smaller particles having sizes which do not pose a problem in relation to clogging.

Although the invention is described with reference to the processing of "biomass" in general, the invention is particularly intended for use in relation with a lignocellulosic biomass. Any suitable lignocellulosic biomass may be used, including soft lignocellulosic biomasses, such as at least wheat straw, corn stover, corn cobs, empty fruit bunches, rice straw, oat straw, barley straw, rye straw, canola/rape straw, sorghum, sweet sorghum, soybean stover, switch grass, Bermuda grass and other grasses, sugar cane bagasse, beet pulp, corn fiber, or any combinations thereof. Hard lignocellulosic biomass may also be used including at least hardwood, softwood, wood pulp, and forestry wastes. Lignocellulosic biomass may be used as a mixture of materials originating from different feedstock, may be fresh, partially dried, fully dried or any combination thereof.

BRIEF DESCRIPTION OF THE DRAWINGS

FIG. 2b shows a top view of the discharge device according to FIG. 2a.

FIG. 5a illustrates at a given time in a steady-state situation of the use of a prior art hydrocyclone having no means for agitation, the temperature gradient of the internal of that hydrocyclone.

FIG. 5b illustrates at a given time in a steady-state situation of the use of the discharge device according to the present invention, the temperature gradient of the internal of the vessel of that device.

DETAILED DESCRIPTION OF THE INVENTION

Figure 1:
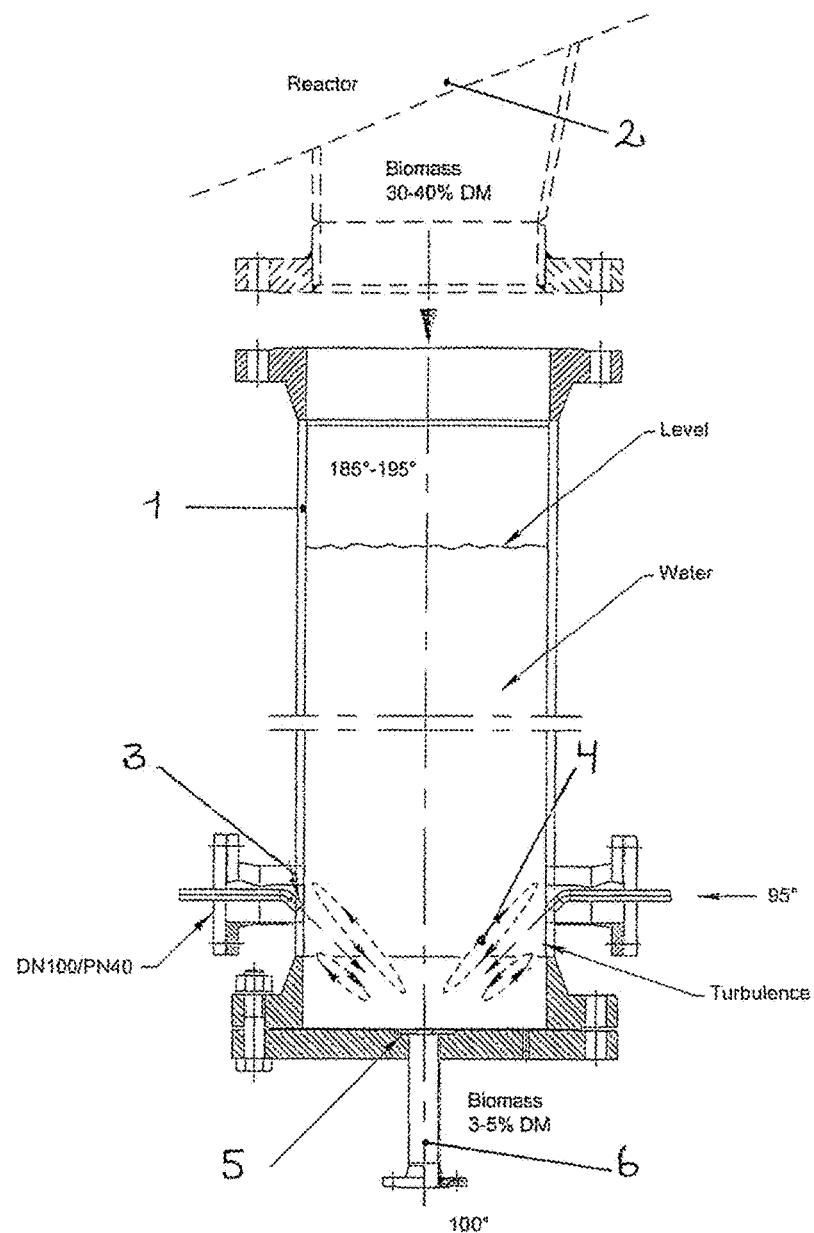
FIG. 1 shows a side view of a prior art device according to WO 2009/147512 A2 for discharging biomass that has been subject to pressurized treatments into lower or atmospheric pressure regions.

The Discharge Device According to the Present Invention

The present invention relates to a discharge device for discharging pretreated biomass from higher to lower pressure, said discharge device in the orientation intended for use comprising:
- a vessel having an opening to a high pressure region at the top, and configured to be connected with a pressurized biomass pretreatment device;
- one or more inlet openings situated along the sides of the vessels through which water or liquid may be added;
- an orifice or valve at a lower part of said vessel, said orifice or valve being configured to eject pretreated biomass, optionally into a pipeline.

The discharge device according to the present invention is characterised in that that the discharge device comprises mechanical agitation means, said agitation means comprising an agitation element arranged in the interior of said vessel at a lower part of said vessel, and being configured to provide agitation of the content of said vessel, wherein said agitation means being adapted to withstand a pressure in the interior of a said vessel of 10 bar or more.

Accordingly, the discharge device of the of the present invention comprises a vessel having an opening for receiving pretreated biomass, one or more opening for supplying liquids and an output port at a lower end of said vessel for ejecting pretreated biomass which by passing through the vessel has been cooled to a temperature allowing transfer into an atmospheric environment. The vessel comprises mechanical agitation means, which in turn comprises an agitation element arranged in the interior of said vessel at a lower part of said vessel. The mechanical agitation means will be responsible for at least partly breaking down a temperature stratification or gradient encountered by the liquid or slurry present in the vessel during use, as it was previously known from WO2009/147512 A2.

By breaking down the temperature stratification or temperature gradient, which would otherwise be present without the inclusion of the mechanical agitation means, an equalization of temperatures within a specific vertical range of heights of the aqueous slurry present in said vessel will occur in such a way that there exists a vertical range of heights, in said aqueous slurry in respect of which the variation of temperatures has a specified upper limit.

In the present description and in the appended claims the term "the orientation intended for use" shall be construed to mean in the orientation in which the device is suitable for discharging said pretreated biomass.

In the present description and in the appended claims the term "lower part of the vessel" shall be construed to mean the lower half, preferably the lower third of the vertical height of the interior of said vessel.

In one embodiment of the present invention, said vessel is an essentially upright oriented vessel.

As the hot pretreated biomass is entering in the top of the vessel and exiting at a lower end, and as the purpose of the vessel is to reduce the temperature of the biomass it is advantageous to make the vessel have a larger extension in a vertical direction compared to the horizontal direction, thus providing a maximum distance in a vertical direction for allowing the biomass to attain a lower temperature.

In one embodiment of the device of the present invention, said vessel is substantially cylindrical or conical.

The vessel itself is preferably substantially cylindrical or conical and may be of any size suited to the volume of use required. As used herein, the term "substantially cylindrical or conical" includes any combination of cylindrical and conical portions. For example, a vessel that is cylindrical in the top portion and conical in the bottom portion is substantially cylindrical or conical as used herein. The term "diameter of the vessel" as used herein refers to the widest diameter.

Preferably, the vessel and said agitation means being adapted to withstand a pressure in the interior of a said vessel of 10 bar or more, such as 12 bar or more, for example 14 bar or more, e.g. 16 bar or more, for example 18 bar or more, e.g. 20 bar or more, like 22 bar or more, such as 24 bar or more, for example 26 bar or more, e.g. 28 bar or more, or 30 bar or more.

In other embodiments it has been found that it suffices that said agitation means being adapted to withstand a pressure in the interior of a said vessel of 6-8 bar or more.

In one embodiment of the discharge device of the present invention said mechanical agitation means comprises drive means and an agitation element, wherein said drive means providing mechanical movement to said agitation element via a connecting element, such as an axle, wherein said agitation element is arranged in the interior of said vessel, and wherein said drive means is arranged at the exterior of said vessel; wherein said agitation element and said drive means are being separated by a sealing.

It may be preferred to design the mechanical agitation means in such a way that the drive means, such as an electric motor, is arranged outside the interior of the vessel, whereas the agitation element providing the mechanical movement of the content of the vessel obviously must be present in the interior of the vessel.

By providing the drive means, such as an electric motor, outside the interior of the vessel, any maintenance may be easily performed. Further, as the drive means may constitute delicate equipment, more protection to this equipment is provided outside the vessel, compared to inside the vessel. In such embodiment a sealing provides sufficient separation between the interior and the exterior of the vessel.

In one embodiment of the discharge device of the present invention said sealing is adapted to withstand a pressure difference between the drive means and the agitation element of 10-52 bar, such as 12-50 bar, for example 14-48 bar, such as 16-46 bar or 18-44 bar, such as 20-42 bar, for example 22-40 bar, such as 24-38 bar, for example 26-36 bar, such as 28-34 bar, for example 30-32 bar.

These ranges of pressure requirements to the sealing will be sufficient for the typical transfer of a hydrothermally pretreated lignocellulosic biomass from a high pressure region in a pretreatment reactor to the vessel according the present invention.

By the term "adapted to withstand a pressure difference" as used in the present description and in the appended claims shall be understood that under the specified pressure differences, the sealing does not leak any material from a high pressure side of the sealing to a low pressure side of the sealing.

In one embodiment of the discharge device of the present invention said sealing being provided with means for cooling, such as means for water cooling.

In one embodiment of the discharge device of the present invention said agitation element is in the form of a rotor comprising a conical screw, a propeller, one or more blades, or a spiral.

This type of agitation element has proved beneficial for the intended purpose of mechanically stirring a pretreated biomass.

A conical screw has been found especially sell-suited for this purpose. It will be preferred that in case the agitation element is in the form of a conical screw, the direction of rotation will be such that biomass will be sucked in a direction from a point located in an axially distance from the tip of the screw in the interior of the vessel and towards the tip of that screw. However, the opposite direction of rotation will also be possible.

In one embodiment of the discharge device of the present invention the vessel has an internal volume of 500 l or more, such as 1000 l or more, for example 2000 l or more, such as 5000 l or more, e.g. 10,000 l or more, such as 15,000 l or more, or 20,000 l or more.

Such volumes have proven suitable for a typically-sized pre-treatment reactor of second generation bioethanol production plant.

In one embodiment of the discharge device of the present invention the power of said drive means in relation to the interior volume of said vessel is 1.5-8.0 kW/m$^3$, such a s 2.0-7.5 kW/m$^3$, e.g. 2.5-7.0 kW/m$^3$, such as 3.0-6.5 kW/m$^3$, such as 3.5-6.0 kW/m$^3$, such as 4.0-5.5 kW/m$^3$, for example 4.5-5.0 kW/m$^3$.

Such powers have proven suitable for providing sufficient agitation of the content of the vessel of the discharge device according to the present invention.

In embodiment of the discharge device of the present invention said agitation element being adapted to provide, during use of said device, an equalization of temperatures within a specific vertical range of heights of an aqueous slurry present in said vessel in such a way that there exists a vertical range of heights, H of 40 cm or more in said aqueous slurry in respect of which the variation of temperatures, ΔT of said slurry is 30° C. or less.

The above values of H and ΔT can be interpreted as expressions of the capability of the device to equalize the temperature of the content of the vessel; the higher the value of H and the lover the value of ΔT, the higher the capability of the device to equalize the temperature of the content of the vessel.

In the present description and in the appended claim, the term "equalization" shall not be construed as "bringing all matter to the exact same temperature" in a mathematical sense. Rather, the term shall be interpreted as meaning that the temperature differences of the content at various heights of the vessel are considerably reduced.

In one embodiment of the discharge device of the present invention said vertical range of heights, H independently is 40-95 cm, such as 45-90 cm, for example 50-85 cm, such as 55-80 cm, e.g. 60-75 cm, such as 65-70 cm.

In one embodiment of the discharge device of the present invention the variation of temperatures, ΔT of said slurry independently is 0-30° C., such as 2-28° C., for example 4-26° C., such as 6-24° C., such as 8-22° C., for example 10-20° C., e.g. 12-18° C., such as 14-16° C.

These ranges of the vertical range of heights, H, and the variation of temperatures, ΔT have proven sufficient and appropriate for the intended purpose. The requirement of the embodiment that during use the agitation element being adapted to provide the temperature equalisations set out above shall in the present description and in the appended claims mean that for any given size and geometry of a device according to the present invention, when used for continuously adding lignocellulosic biomass that has been subject to pressurized pretreatment at a temperature of 160-210° C. in order to bring that biomass into lower or atmospheric pressure regions, when in a "steady state" situation in which an aqueous slurry is removed at the orifice or valve at the bottom and recirculated to an inlet opening, optionally with removal of fibrous biomass, there exist a vertical range of heights, H of the indicated size in said aqueous slurry in respect of which the variation of temperatures, ΔT of said slurry is as indicated.

This limitation of temperature variation in the aqueous slurry is especially valid in case the vessel is having a volumetric fill level of 30-50% of a biomass, preferably a lignocellulosic biomass, such as wheat straw, cut to an average length of 40 mm, wherein the dry matter content of fibres of the aqueous slurry is within the range of 4-11 wt %, such as 5-10 wt %, for example 6-9 wt % or 7-8 wt %, and wherein the degree of recirculation lies within the range of 14-18%, such a s 15-16%.

Hence, this requirement expresses the ability of the agitation element and associated agitation means to provide a stirring in the aqueous slurry that will result in the desired equalization of temperatures.

In the present application a degree of recirculation is defined as the amount of liquid being added (as measured in cubic meters) via the one or more inlet opening in relation to the dry matter weight of biomass added (as measured in tonnes) via the opening at the top.

In an another and alternative embodiment which applies generally irrespective of the internal volume and/or of the internal height of the vessel of the discharge device according to the present invention, said agitation element being adapted to provide, during use of said discharge device, an equalization of temperatures within a specific vertical range of heights of an aqueous slurry present in said vessel in such a way that there is a vertical temperature gradient of 50° C./meter or less, such as 45° C./meter or less, for example 40° C./meter or less, e.g. 35° C./meter or less, such as 30° C./meter or less, for example 25° C./meter or less; or 20° C./meter or less. Said vertical temperature gradient preferably applies in respect of a vertical range of heights H, in said aqueous slurry of 10 cm or more, such as 15 cm or more, e.g. 20 cm or more, for example 25 cm or more; or 30 cm or more. Said vertical temperature gradient preferably being present in an upper half, such as an upper third of the slurry content of the vessel.

In one embodiment of the discharge device of the present invention said discharge device furthermore comprises a conduit connecting one or more of the inlet openings to said orifice or valve at the lower part of said vessel, thereby forming a loop for recirculation of liquid or slurry.

In one embodiment of this embodiment this loop for recirculating liquid or slurry comprises means for separation of pretreated biomass from said liquid.

In one embodiment of the discharge device of the present invention said means for separation of pretreated biomass from said liquid comprises a press, such as a screw press, e.g. a single or a twin screw press, a belt press, a drum filter, a centrifuge or a decanter centrifuge.

The provision of the discharge device with a conduit connecting one or more of inlet openings to said orifice or valve at the lower part of said vessel, thereby forming a loop, allows for recirculation of liquid or slurry. This means reuse of a liquid fraction originating from the pretreatment reactor and thus savings in the amount of fresh water used.

Providing this loop for recirculating liquid or slurry with means for separation of pretreated biomass from said liquid allows for isolating the biomass for further downstream processing.

It should be noted that a mixture of fresh water or liquid, such as water, originating from any source other than the pretreatment reactor, may be supplied to one or more of said inlet openings in the vessel.

In one embodiment of the discharge device of the present invention said vessel comprises one or more sensors for monitoring physical and/or chemical characteristics of the content of said vessel, said sensors being selected from the group comprising: temperature sensors, NIR-sensors, pH-sensors, electric conductivity sensors, microwave sensors for detecting dry matter content, one or more sensors for detecting height of level of slurry or liquid, such as gamma sensors or differential pressure sensors.

In one embodiment of this embodiment the vessel comprising a control unit for controlling operation of said device, at least partly based on information representing readings from one or more of said sensors.

In one embodiment of the discharge device of the present invention, said opening to a high pressure region at the top of the vessel, being configured to be connected with a pressurized biomass pretreatment device, is adapted to allow biomass to enter said device by falling by gravity, vertically from said opening into said vessel.

In one embodiment of the discharge device of the present invention, said opening to a high pressure region at the top of the vessel is having a cross-sectional area of 0.2-8 $m^2$, such as 0.5-7 $m^2$, for example 1-6 $m^2$, such as 2-5 $m^2$ or 3-4 $m^2$.

As the biomass intended for processing with the device according to the invention may be very viscous and comprises elongated material such as straws and the like which may be intertwined it is important that the vessel allows the biomass to enter the interior in a safe and efficient way without any risk of obstructing the opening at the top. The above two embodiments allows for this In one embodiment of the discharge device of the present invention, said vessel in use is adapted to allow liquid, solids and steam to exit the vessel by the same exit route(s).

It is preferred that the vessel of the discharge device in use is adapted to allow liquid, solids and steam to exit the vessel by the same route(s). It is preferably advantageous that the vessel does not comprise means for separating the content of the vessel into different fractions, such as a steam fraction, a solid fraction and a liquid fraction, where one or more fraction exiting via its own exit route.

The Apparatus According to the Present Invention

The present invention also relates to an apparatus. The apparatus according to the present invention comprises a discharge device according to the present invention in combination with a hydrothermal pretreatment reactor;

wherein said hydrothermal pretreatment reactor comprising a cylinder being essentially horizontally arranged and having an inlet for biomass at a first axial end and an outlet for biomass at a second axial end, opposite to said first end;

wherein said cylinder comprises in its interior a rotatable auger screw, said auger screw being configured for conveyance of biomass from said first axial end to said second axial end;

wherein said cylinder furthermore comprises one or more inlets for steam and/or water;

wherein said outlet for hydrothermally pretreated biomass at a second axial end of said cylinder being connected to said opening arranged at the top of the vessel of said discharge device.

In one embodiment of the apparatus according to the present invention, said apparatus comprises an array of consecutively arranged cylinders, each cylinder being essentially horizontally arranged and having an inlet for biomass at a first axial end and an outlet for biomass at a second axial end opposite to said first end;

wherein each said cylinder comprises in its interior a rotatable auger screw, said auger screw being configured for conveyance of biomass from said first axial end to said second axial end of said cylinder;

wherein in respect of each cylinder, the outlet at a second axial end of said cylinder is connected to said inlet at a first axial end of a subsequent cylinder by a connection element;

wherein in respect of the last cylinder in the array of consecutively arranged cylinders, the outlet of said last cylinder is being connected to said opening arranged at the top of the vessel of said discharge device.

In one embodiment of the apparatus according to the present invention, said array of consecutively arranged cylinders comprises 2-7, such as 3-6 for example 4-5 cylinders.

Using an array of cylinders in the hydrothermal pretreatment reactor provides for allowing processing biomass at various thermal and chemical degrees of severities. Furthermore, an array of cylinders may save ground space compared to a single cylinder having a volume corresponding to the sum of volumes of an array of cylinders.

In one embodiment of the apparatus according to the present invention, each cylinder being arranged on top of its successive cylinder;

wherein each connection element, connecting a cylinder with its successive cylinder, being essentially vertically arranged, thereby allowing a free fall of biomass in its transition from one cylinder to its successive cylinder The free falling of the biomass between each cylinder of the hydrothermal pretreatment reactor provides for mixing the biomass and thus a better heat transfer and a more homogeneous heating.

The Use According to the Present Invention

The present invention also relates to a use of a discharge device according to the invention for transferring a pretreated biomass from higher to lower pressures.

In one embodiment this use relates to the purpose of suppressing the loss of C5-saccharides, such as xylan species, from the biomass into an aqueous phase during said transfer.

In another embodiment this use relates to the purpose of suppressing the formation and transfer of furfural into the liquid phase.

In yet another embodiment this use relates to limiting the adverse effects of deposition of re-solidified lignin.

The Method According to the Present Invention

The present invention finally relates to a method for discharging biomass from higher to lower pressure. This method comprises:

i) loading pretreated biomass originating from a higher pressure environment into an upper end of a vessel so as to obtain in said vessel a lower aqueous slurry comprising biomass and an upper gaseous fraction;

ii) performing a mechanical agitation of said aqueous slurry in the lower part of said vessel by means of a mechanical agitation element arranged in the interior of said vessel;

iii) supplying a stream of aqueous liquid into the vessel;

iv) unloading aqueous slurry comprising pretreated biomass from a lower part of said vessel.

In one embodiment of the method of the present invention, the vessel is an essentially upright oriented vessel.

As the hot pretreated biomass is entering in the top of the vessel and exiting at a lower end, and as the purpose of the vessel is to reduce the temperature of the biomass it is advantageous to make the vessel have a larger extension in a vertical direction compared to the horizontal direction, thus providing a maximum distance in a vertical direction for allowing the biomass to attain a lower temperature.

In one embodiment of the method of the present invention the degree of mechanical agitation of said aqueous slurry is controlled in a way to ensure an equalization of temperatures within a specific vertical range of heights of said aqueous slurry in such a way that there exists a vertical range of heights, H of 40 cm or more in said aqueous slurry in respect of which the variation of temperatures, ΔT of said slurry is 30° C. or less.

The above values of H and ΔT can be interpreted as expressions of the capability of the device to equalize the temperature of the content of the vessel; the higher the value of H and the lover the value of ΔT, the higher the capability of the device to equalize the temperature of the content of the vessel.

In one embodiment of the method of the present invention said vertical range of heights, H independently is 40-95 cm, such as 45-90 cm, for example 50-85 cm, such as 55-80 cm, e.g. 60-75 cm, such as 65-70 cm.

In one embodiment of the method of the present invention said variation of temperatures, ΔT of said slurry independently is 0-30° C., such as 2-28° C., for example 4-26° C., such as 6-24° C., such as 8-22° C., for example 10-20° C., e.g. 12-18° C., such as 14-16° C.

These ranges of the vertical range of heights, H, and the variation of temperatures, ΔT have proven sufficient and appropriate for the intended purpose.

In an another and alternative embodiment of the method according to the present invention which applies generally irrespective of the internal volume and/or of the internal height of the vessel of the discharge device used with the method, an equalization of temperatures within a specific vertical range of heights of an aqueous slurry present in said vessel is established in such a way that there is a vertical temperature gradient of 50° C./meter or less, such as 45° C./meter or less, for example 40° C./meter or less, e.g. 35° C./meter or less, such as 30° C./meter or less, for example 25° C./meter or less; or 20° C./meter or less. Said vertical temperature gradient preferably applies in respect of a vertical range of heights H, in said aqueous slurry of 10 cm or more, such as 15 cm or more, e.g. 20 cm or more, for example 25 cm or more; or 30 cm or more. Said vertical temperature gradient preferably being present in an upper half, such as an upper third of the slurry content of the vessel.

In one embodiment of the method of the present invention said method is a continuous process.

A continuous process is preferred because it provides for a more efficient processing.

As previously mentioned the purpose of subjecting a lignocellulosic biomass to a hydrothermal pretreatment in a second generation bioethanol plant is to loosen up the polymer structure comprising cellulose, hemicellulose and lignin in order to make the cellulose more accessible for enzymes in an enzymatic hydrolysis in a subsequent processing step.

The harshness of the hydrothermal pretreatment is a function of temperature and time; the longer time, a lignocellulosic biomass is subjected to a hydrothermal pretreatment, the more accessible the cellulose will become for enzymatic attack. Likewise, the higher temperature in the hydrothermal pretreatment, the more accessible the cellulose will become for enzymatic attack.

In order to be able to better compare the harshness of various combinations of temperature and treatment times in hydrothermal pretreatments of lignocellulosic biomass, a severity index has been introduced.

The severity index is defined (in case no acids or bases are added in the hydrothermal pretreatment) as:

$$\text{Severity} = Ro = t_r \exp[(T_r - 100)/14.75],$$

wherein $t_r$ being the reaction time of the pretreatment, measured in minutes, and wherein $T_r$ being the reaction temperature of the pretreatment, measured in degrees centigrade. Usually, the severity is given as the log severity.

The device, the apparatus, the use and the method according to the present invention is suitable for discharging biomass, such as lignocellulosic biomass, which has been pretreated at a log severity of 3.3-4.3, such as a log severity of 3.4-4.2, for example a log severity of 3.5-4.1, such as a log severity of 3.6-4.0, for example a log severity of 3.7-3.9.

However, the severity factor representing the degree of pretreatment which makes the cellulose accessible for enzyme attack has a side effect in that the pretreatment corresponding to this severity factor also is responsible for degradation of hemicellulose present in the biomass into degradation products, such as various carboxylic acids.

Accordingly, rendering the cellulose accessible for enzyme attack and thereby allowing formation of glucose in a subsequent hydrolysis step comes at the price of losing hemicellulose present in the biomass into degradation products.

In some instances, for example in case the biomass to be processed is intended for use in a fermentation process for fermentation into ethanol or other chemicals, wherein microorganisms ferment glucan and hemicellulose into the desired product(s) it is desirably that the loss of hemicellulose, originating from the biomass, into degradation products, is less than 40 wt %, such as less than 35 wt %, for example less than 30 wt %, such as less than 25 wt % or less than 20 wt %, compared to the content of hemicellulose originally present in the biomass prior to the hydrothermal pretreatment.

In other instances, for example in case the biomass to be processed is intended for use in a fermentation process for fermentation into ethanol or other chemicals, wherein microorganisms ferment only glucan into the desired product(s) it is acceptable that the loss of hemicellulose, originating from the biomass, into degradation products is 40 wt % or more, such as 45 wt % or more, for example 50 wt % or more, such as 55 wt % or more, such as 60 wt % or more, for example 75 wt % or more, or even 80 wt % or more, compared to the content of hemicellulose originally present in the biomass prior to the hydrothermal pretreatment.

In one embodiment of the method of the present invention said pretreated biomass is ejected into a pipeline and driven by pressure drop to further processing steps.

In one embodiment of the method of the present invention said pretreated biomass is ejected as a slurry that is subsequently pressed in order to recover water which is subsequently recycled.

In one embodiment of the method of the present invention, said pretreated biomass being ejected as a slurry is subsequently pressed in order to recover a fibre fraction of said biomass.

In one embodiment of this embodiment, the fibre fraction of said biomass is recovered using a mean for separation of pretreated biomass from liquid, wherein said mean for separation of pretreated biomass is selected from the group comprising: a press, such as a screw press, e.g. a single or a twin screw press, a belt press, a drum filter, a centrifuge or a decanter centrifuge.

As the fibre fraction comprises valuable carbon sources, it is desirable to separate this fibre fraction from the liquid phase.

In one embodiment of these embodiments, water or aqueous medium is recovered in the separation, and optionally being returned to said vessel in step iii) in order to recycle such water or aqueous medium.

Recycling of water or aqueous medium saves cost in the method.

In one embodiment of the method of the present invention said biomass has been hydrothermally pretreated by subjecting said biomass to elevated pressures and temperatures; wherein said hydrothermal pretreatment of said biomass has been conducted without addition of any acids, bases or other chemical, other than water or steam, In one embodiment, said biomass, which is being loaded into an upper end of said vessel, prior to its hydrothermal pretreatment has been subjected to a soaking operation in an aqueous medium, wherein said aqueous soaking medium does not contain acids, bases or other added chemicals except water; or wherein said soaking medium comprises process water or aqueous medium having a pH of 3.0-7.5, such as pH 3.5-7.0, for example pH 4.0-6.5, such as pH 4.5-6.0 or pH 5.0-5.5.

In one embodiment of the method of the present invention said biomass is a lignocellulosic biomass.

A lignocellulosic biomass which has been hydrothermally pretreated is particularly well-suited for use with the method of the present invention.

In one embodiment of the method of the present invention, said biomass has been subjected to a hydrothermal pretreatment at a log severity of 3.3-4.3, such as 3.4-4.2, for example 3.5-4.1, e.g. 3.6-4.0, such as 3.7-3.9.

In the method of the present invention the mechanical agitation of the aqueous slurry may be performed by a mechanical agitation means comprising an agitation element driven by a drive means, such as disclosed in respect of the device according to the present invention.

In one embodiment of the method of the present invention, the method is conducted by using a discharge device according to the present invention; ort by using an apparatus according to the present invention.

Referring now in details to the drawings for the purpose of illustrating the present invention, FIG. 1 shows a side view of a prior art device for discharging biomass that has been subject to pressurized treatments into lower or atmospheric pressure regions. As shown, the device comprises a cylindrical discharge vessel 1 and has an opening 2 to a high pressure region at the top, through which pretreated biomass is added. During use, the vessel is partially filled with water or aqueous solution and is fitted with nozzles 3. Introduction of water or aqueous solution through the nozzles 3 establishes turbulence 4 around the outlet orifice 5. The outlet orifice 5 is in communication with a pipeline 6 through which ejected, pretreated biomass can be transported.

In the prior art device shown in FIG. 1, a plurality of water nozzles or jets are situated on the sides of the discharge vessel. These nozzles or jets provides for establishing a vortex in the bottom part of the vessel. Water or other liquid are injected through these nozzles or jets in such manner as to establish such a vortex in the lower part of the vessel. Typically, the temperature of the water or liquid injected through these nozzles or jets is slightly lower than boiling temperature.

At least one outlet orifice or valve at the bottom of the vessel secures a drop in pressure as the water/biomass mixture is ejected at high speed, for example into a pipeline that carries the mixture to further processing steps.

In the prior art device depicted in FIG. 1 the addition of liquid through the nozzles will create a turbulence 4 in the liquid phase of the content of the vessel. This turbulence results in the establishment of temperature stratification of the liquid phase. This means that a temperature gradient will be present in the liquid; having relatively high temperatures at a top position and gradually decreasing temperatures at lower positions.

Although the prior art device shown in FIG. 1 provides for a convenient transfer from a high to a low pressure region of a lignocellulosic biomass which has been pretreated at high temperatures, this prior art device nevertheless does not provide for an optimum utilisation of the sugars present in the fibrous biomass, in that it has been found that when using this device for processing pretreated lignocellulosic biomass, valuable C5 sugars initially present in the fibrous lignocellulosic biomass are lost into the liquid phase.

Figure 2A:
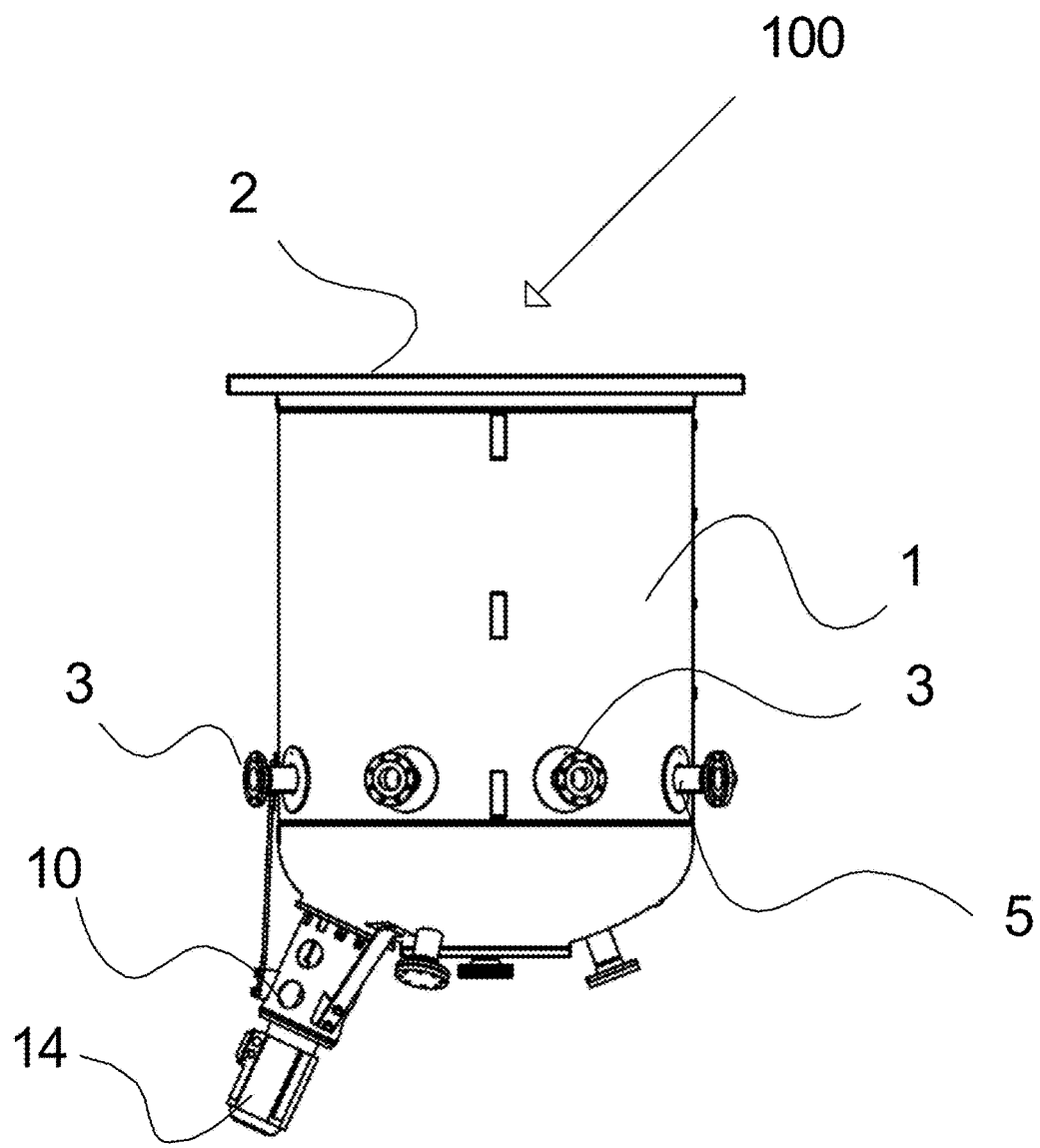
FIG. 2a shows a side view of a discharge device according to a the present invention for discharging biomass that has been subject to pressurized treatments into lower or atmospheric pressure regions.

FIG. 2a shows a side view of an embodiment of a discharge device 100 according to the present invention. FIG. 2a shows that the discharge device 100 comprises a cylindrical discharge vessel 1 which in this case is vertically oriented. The vessel comprises a top end and a bottom end. In the top end is arranged an opening 2 to a high pressure region, through which pretreated biomass may be added. In a lower end are arranged a number of inlet openings 3 for supplying liquid. In a lower part of the device are located an orifice or valve 5 configured to eject pretreated biomass, optionally into a pipeline.

In some embodiments, the discharge vessel is fixed with pressurized sealing directly to a pressurized biomass pretreatment device. Alternatively, a pressurized biomass pretreatment device may be communicated to the discharge vessel by pipes or other means of conveyance.

Furthermore, FIG. 2a shows that the discharge device is provided with mechanical agitation means 10. The mechanical agitation means 10 comprises in this case an agitation element 16 in the form of a conical screw arranged in the interior of said vessel at a lower part of said vessel (not shown in FIG. 2a). The agitation element is configured to provide agitation of the content of said vessel.

The mechanical agitation means 10 furthermore comprises drive means 14. The drive means is in the form of an electrical motor which may provide mechanical movement to said agitation element 16 via a connecting element 18 in the form of an axle (not shown in FIG. 2a).

As seen in FIG. 2a the drive means 14 is arranged at the exterior of said vessel. The agitation element and said drive means are being separated by a sealing.

The vessel 1 itself is preferably substantially cylindrical or conical and may be of any size suited to the volume of use required. As used herein, the term "substantially cylindrical or conical" includes any combination of cylindrical and conical portions. For example, a discharge vessel that is cylindrical in the top portion and conical in the bottom portion is substantially cylindrical or conical as used herein. In preferred embodiments, the discharge vessel is suitable for use in production-scale biomass pretreatment and has a volume of at least 500 liters, or at least 700 liters, or at least 2000 liters.

As used herein the "top" of the discharge vessel is the end connected with a pressurized biomass pretreatment device where the "bottom" is the end from which biomass is ejected. The orifice or valve through which biomass is ejected may be a single opening or multiple openings clustered in one general area. In some embodiments, more than one outlet orifice or valve may be used.

In use, the discharge vessel is filled with a quantity of water or aqueous solution, preferably comprising between about ½ to about ⅔ of its total internal volume. In some embodiments, the discharge vessel may be filled to ⅘ of its total internal volume. In alternative embodiments a lower filling level is desired. However, it is preferred that the filling level exceeds the vertical position of the inlet openings situated along the sides of the vessel so that steam does not have direct access to these opening.

Biomass is added at the top of the vessel at high temperature, typically between 160-210° C., and at high pressure, typically between 5 and 25 atmospheres. Ideally, the pretreated biomass should have sufficient density and/or other properties as to sink in the water or aqueous solution within the discharge vessel. In some cases, it may be advantageous to adjust the size of very long particles, such as grasses or straws, in order to achieve fast sedimentation.

As seen in FIG. 2a a plurality of inlet openings 3 are situated on the sides of the discharge vessel. The inlet openings are preferably situated at a lower part of the vessel. These inlet openings 3 serve the purpose of adding water of aqueous liquid which will result in a cooling of the hot content of the vessel.

Although the presence of only a single inlet opening is possible, it is preferred to provide the vessel with a plurality of such inlet openings, such as 2, 3, 4, 5, 6, 7 or 8 inlet openings.

The water or liquid injected through these inlet openings is preferably slightly lower than boiling, preferably about 95° C.

In preferred embodiments, the discharge vessel is oriented substantially vertically and the biomass sinks in the liquid to the bottom of the vessel. Alternative embodiments can comprise a more horizontal orientation of the discharge vessel. At least one outlet orifice or valve 5 at the lower part of the vessel secures a drop in pressure as the water/biomass mixture is ejected at high speed, preferably into a pipeline that carries the mixture to further processing steps. The pressure drop alone is sufficient to drive the water/biomass mixture through a pipeline.

Because the water in the pressurized region is at a temperature above boiling, compared with the pressure in other parts of the system, a mixture of biomass and water ejected from the discharge vessel may contain fine steam bubbles which help ensure that transport of biomass through a pipeline will be without blockage.

Water/biomass mixture leaving the vessel typically release some steam due to flash evaporation on entering a lower pressure zone. In preferred embodiments, after transport through a pipeline to subsequent processing steps, the biomass is filtered from the water. Biomass may accordingly be pretreated at high dry matter, diluted into a slurry during discharge, then filtered back to an appropriate dry matter content for further processing. Water filtered from the slurry can be, in turn, recovered and recirculated back into the discharge vessel.

The liquid at the top of the discharge vessel is very hot, where heat is introduced by steaming biomass. At the bottom of the vessel, however, the liquid is comparatively cool.

Figure 2B:
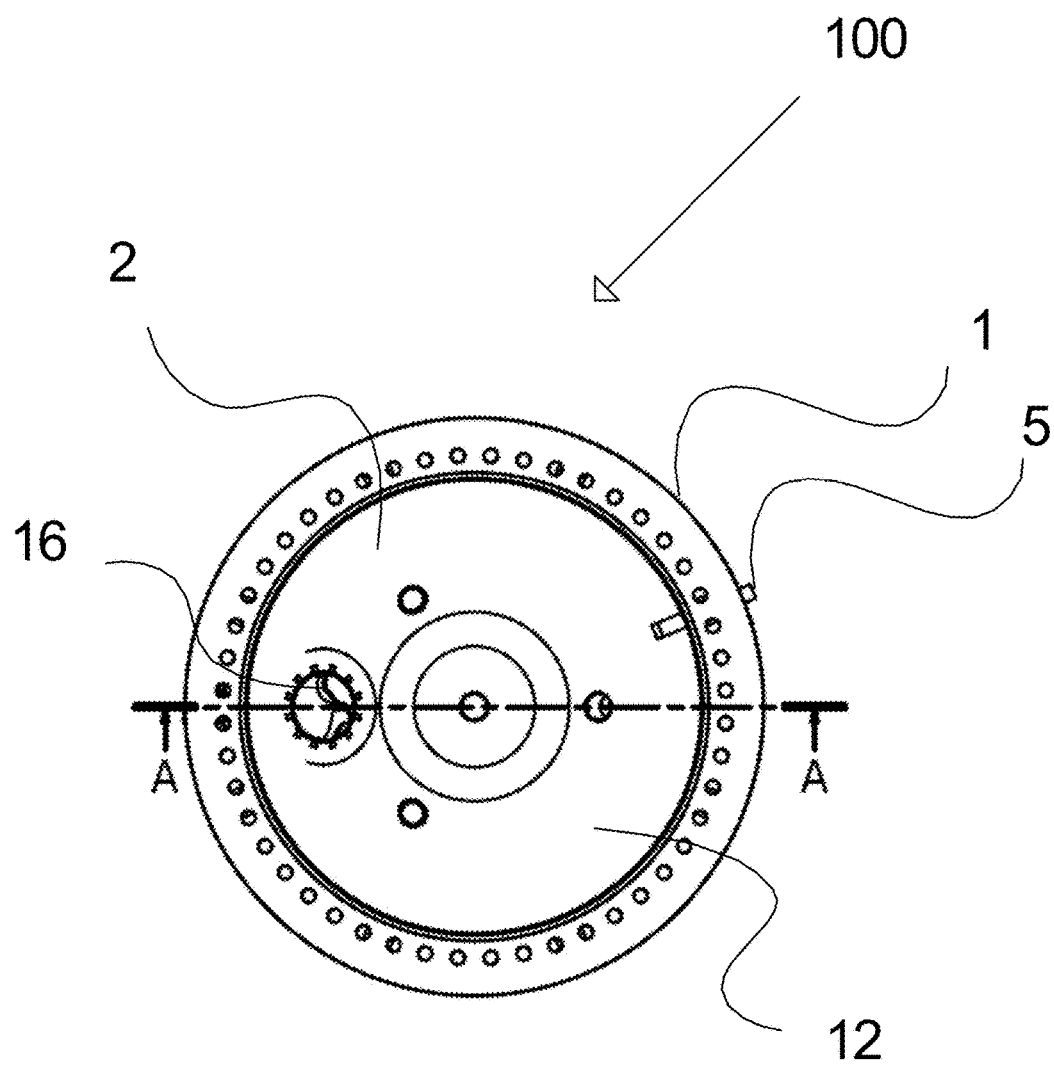

FIG. 2b is a top view of the device shown in FIG. 2a. Accordingly, FIG. 2a shows the discharge device 100 as seen into the opening 2 of the top of the device. FIG. 2b shows the outlet orifices 5 and that the agitation element 16 of the mechanical agitation means is arranged in the interior 12 of that vessel. The agitation element 16 is in this case a in the form of a conical screw arranged in the interior of said vessel at a lower part of said vessel.

Figure 2C:
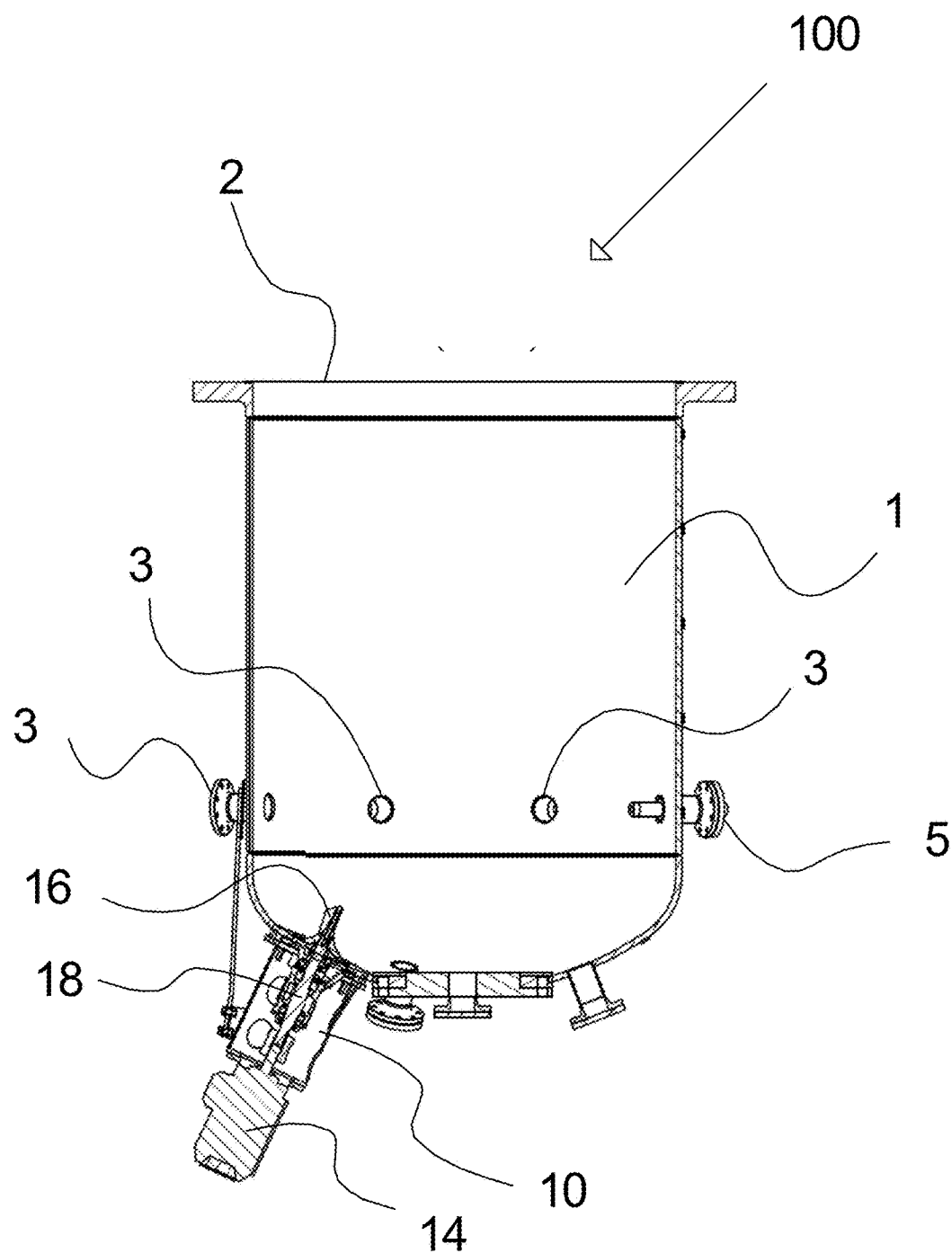
FIG. 2c shows a cross-sectional view of the discharge device according to FIG. 2b.

FIG. 2c is a cross-sectional view as seen at the cut A-A of FIG. 2b. In FIG. 2c are seen the opening 2 at the top of the vessel, the inlet openings 3 for supplying liquid as well as outlet orifices 5. Furthermore, the various elements of the mechanical agitation means 10 are shown to comprise drive means 14 in the form of an electrical motor and arranged on the exterior of the vessel, an agitation element 16 in the form of a conical screw and arranged in the interior of the vessel, a sealing providing pressure-proof seal between the interior and the exterior parts of the mechanical agitation means, and a connecting element 18 in the form of an axle connecting the drive means to the agitation element.

The mechanical agitation means comprising an agitation element 16 provides for a relatively violent stirring of the content of the vessel. This stirring of the content of the vessel thereby enables that the stratification or gradient of temperatures which would otherwise be present throughout a vertical distance of the slurry in the vessel (such as encountered with the device according to WO 2009/147512 A2) will be eliminated because the activation of the mechanical agitation means will provide so much movement of the slurry in the vessel that a more or less constant temperature will be present throughout a specific vertical distance of the slurry in the vessel.

It is preferred that the means are provided that will allow for a stepwise or continuously adjustment of the power of the agitation means 10 such that a corresponding stepwise or continuously adjustment of the speed of the agitation element will be possible.

In addition to the fact that less C5 sugars are lost from the biomass into the liquid phase of the content of the vessel, the provision of mechanical agitation means furthermore provides for better temperature control of the device.

In a preferred embodiment the device additionally comprises one or more sensors arranged in the vessel 1, such as temperature sensors, NIR-sensors, pH-sensors, electric conductivity sensors, microwave sensors for detecting dry matter content, one or more sensors for detecting height of level of slurry or liquid, such as gamma sensors or differential pressure sensors.

It is also preferred that the device is provided with a control unit which on the basis of data input from such sensors may control inter alia the orifice or valves 5, the inlet openings 3 and the speed of the agitation element 16.

Preferred embodiments are additionally advantageous in that the design and construction are simple, requiring relatively few mechanical parts and, accordingly, having a long useful life in production.

In typical use of preferred embodiments, the level of water or aqueous solution within the discharge vessel fluctuates. Fluctuations of level may be controlled in some embodiments by adjusting the opening of the outlet orifice or valve and/or the rate of flow introduced through nozzles or jets. In some embodiments, a steady-state level may be maintained by a continuous valve that adjusts the outlet orifice.

In preferred embodiments, a device according to the invention can be used in continuous biomass processing. As used herein, the term "continuous processing" refers to a non-pulsatile, relatively constant flow of feedstock through processing steps.

EXAMPLE

Experiments were performed at the Inbicon demonstration plant in Kalundborg, Denmark.

This example illustrates a process for hydrothermal pretreatment and subsequent discharge of a lignocellulosic biomass into a lower atmospheric pressure region using a prior art hydrocyclone of the type disclosed in WO 2009/147512 A2, however modified by incorporating mechanical agitation means comprising an agitation element arranged in the interior of the vessel of that hydrocyclone in a lower part thereof.

The experiments were performed in two different modes; one mode in which the agitation means were not applied; and another mode in which the agitation means were applied.

Hydrothermal Pretreatment of the Lignocellulosic Biomass

Lignocellulosic biomass in the form of wheat straw (cut to an average length of approximately 40 mm) was continuously loaded onto a reactor for hydrothermal pretreatment of biomass at 185-200° C. for 20 min at a rate of 1500 kg/hour. The reactor comprised a cylinder having its axial axis oriented in a horizontal direction. Within the cylinder a rotatable auger conveyor was suspended which provided an overall horizontal movement of the content of the reactor from one end to the other. During the hydrothermal pretreatment the internal pressure in the reactor was kept within 10-15 bar.

Equalization of Temperature

The temperature equalizations were conveniently performed in a prior art hydrocyclone of the type disclosed in WO 2009/147512 A2 and modified as described above.

The hydrocyclone, in the following denoted "discharge device", consisted of an upright oriented, cylindrical container which at its lower end comprised a round-tapered end cap. The discharge device was at its upper end connected to the hydrothermal reactor from which biomass and water is loaded into the discharge device. The discharge device had an interior height of 2400 mm, an interior diameter in its cylindrical part of 1800 mm and an approximate total volume of 5700 l. Typical filling levels were 2800 l to 3900 l.

Furthermore, the discharge device comprised an outlet for continuous unloading the content of the discharge device, and five inlets for process liquid. The inlets for process liquid were designed in such a way that during operation of the discharge device in a mode in which the agitation means were not applied, the inlet stream of inlet water would create a circulating or stirring movement of the content in the lower part of the vessel of the discharge device. This effect is obtained by making the corresponding inlet nozzle have a slight angling towards the bottom of the vessel of the discharge device.

The circulating or stirring effect provides for creating a temperature gradient within the vessel of the discharge device such that the pretreated biomass present at an upper part of the vessel of the discharge device will have a relative high temperature, whereas the pretreated biomass present at a lower part of the vessel of the discharge device will have a relative low temperature, thus gradually reducing the temperature of the slurry when moving from top to bottom. The discharge device used in this example furthermore comprised a piped loop starting at the outlet of the vessel of the discharge device and comprising conduits making a looping connection with the inlet for process liquid. This piped loop additionally comprised a means for separating solid fibrous matter from liquid.

In this way, during operation of the discharge device, the material exiting the outlet comprises process liquid as well as fibrous lignocellulosic material, whereas the material entering the discharge device via the inlets for process water essentially only comprised liquid.

Process water at a rate of 5-45 m$^3$/h, such as 10-40 m$^3$/h was loaded into the vessel of the device via the inlets for process water.

In order to be able to control the operation of the discharge device a couple of gamma sources and gamma detectors were arranged in the vessel of the discharge device. Furthermore, a differential pressure monitoring system was included in the discharge device. The gamma sources and gamma detectors as well as the differential pressure monitoring system served the purpose of controlling the load level of the vessel of the discharge device.

Temperature sensors where arranged vertically above one another in the vessel of the discharge device at the following vertical positions, zero being the bottom of the vessel discharge device: 650 mm, 880 mm, 1110 mm, 1340 mm, 1570 mm, 1800 mm, 2030 mm, 2260 mm.

The discharge device used in this example was equipped with a mechanical agitation means. The mechanical agitation means comprises an electrical motor of the type Grubbens Rotorenhed 26/26 GHP supplied by Cellwood, Sweden, which was equipped with an agitation element in the form of a conical screw-type rotor arranged in the lower part of the interior of the vessel of said discharge device. The motor was connected to a frequency converter allowing adjustment of the rotational speed.

This mechanical agitation means had an effect of 15 kW.

The motor was arranged on the exterior of the vessel of the hydrocyclone. The motor and conical screw-type rotor were provided with a water cooled sealing capable of withstanding a pressure difference of at least 18 bar.

The hydrothermally treated lignocellulosic material was transferred to the discharge device in a continuous mode as defined by the rotational speed of the screw of the hydrothermal reactor.

During temperature reduction in the discharge device, part of its content was continuously removed via the outlet port. This stream was conducted through a belt press for isolating the hydrothermally pretreated wheat straw. Remaining process water from this fiber press was conducted to one of the inlet ports of the discharge device so as to create a closed loop of circulating process water. The various flows were controlled so as to constantly obtain a loading in the vessel of the discharge device corresponding to a level of approximately 1300-1700 mm.

The continuous process was allowed to run for a number of days and at predetermined intervals samples of liquid as well as biomass were taken out for analysis. During a first part of these runs, the agitation means were not applied, meaning that the agitation means provided no agitation, whereas in later part of these runs, the agitation means indeed were applied, i.e. the agitation means did provide agitation during these latter parts.

During processing of the pretreated biomass in a mode in which the agitation means were not applied, irregularities of the processing in the discharge device were encountered.

These irregularities consisted of formation of a thick layer of slag at the inner lower side of the vessel of the discharge device and concurrently clogging of the outlet port. The clogging and layer formation was probably due to burned lignin forming conglomerates attaching to each other and the inner walls of the vessel of the discharge device.

At the same time it became increasingly difficult to control the discharge device so as to obtain a desired outlet temperature of the slurry of biomass and liquid.

Temperatures at the above defined vertical levels of the aqueous slurry within the vessel were closely monitored during the experiment. These temperature measurements revealed that it was not possible to maintain a satisfactorily stable temperature at a specific height within the vessel of the discharge device.

In the later parts of the runs in which the agitation means were switched on it was evidenced from the temperature measurements that much less pronounced temperature gradient was present in the liquid phase during processing in which the agitator means provided agitation of the biomass slurry. In fact, a rather constant temperature level existed at various levels throughout the lower "wet" phases of the hydrocyclone.

In the later parts of the runs no clogging or build-up of thick layers took place and there were no difficulties in controlling the discharge device so as to obtain a desired outlet temperature of the biomass.

Chemical Analysis and Results

Samples of liquid fraction and fiber fraction were collected at specific intervals during continuous pretreatment.

The fiber fraction from the pretreatment was analysed for carbohydrates according to (Sluiter, Hames et al. 2006, see ref. 6) with an Dionex Ultimate 3000 HPLC system equipped with a Rezex Monosaccharide column from Phenomenex and the liquid fractions were analysed for carbohydrates and degradation products according to (Sluiter, Hames et al. 2005, see ref. 4) with an Dionex Ultimate 3000 HPLC system equipped with a Rezex Monosaccharide column.

Degradation products in the fiber fraction were analysed through suspension of the fiber fraction in water with 5 mM sulphuric acid in an ratio of 1:4 and afterward analysed according to (Sluiter, Hames et al. 2005, see ref. 4) with an Dionex Ultimate 3000 HPLC system equipped with a Rezex Monosaccharide column Phenomenex.

Figure 3:
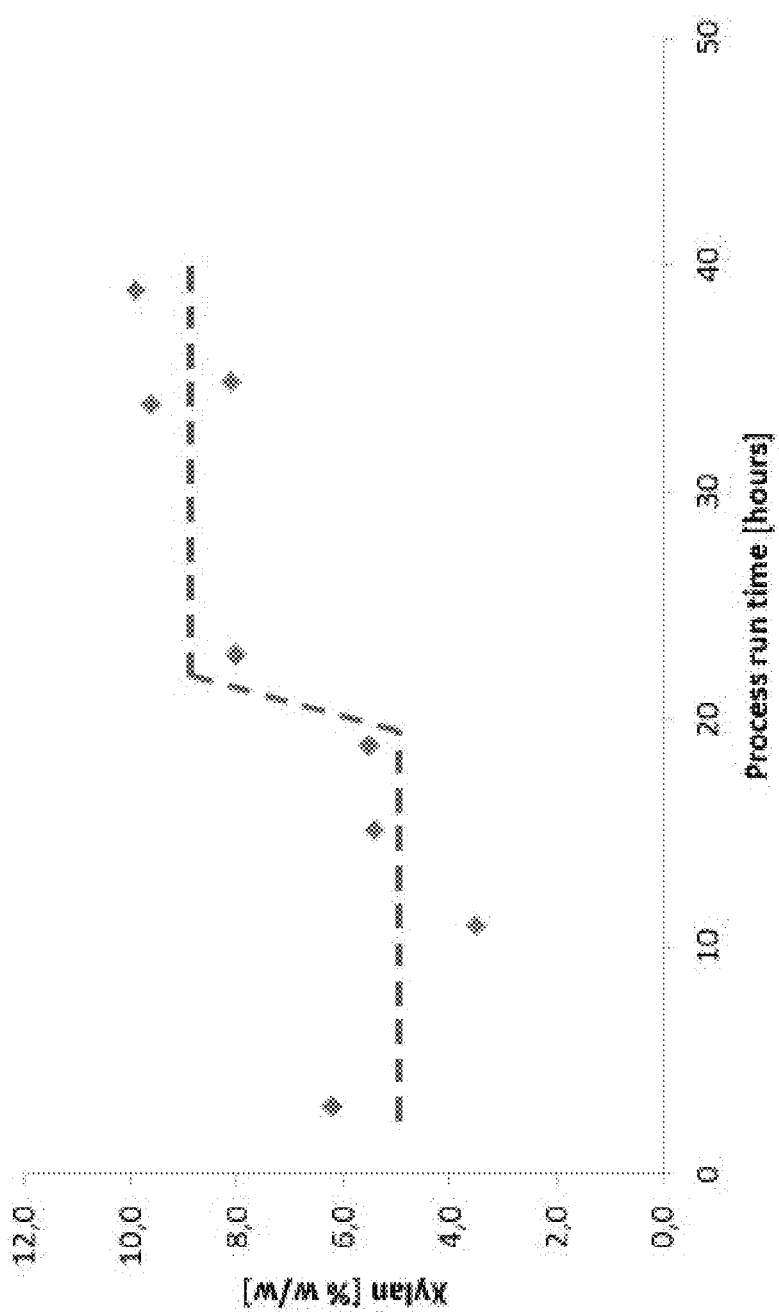
FIG. 3 illustrates xylan content in the solid fraction of a slurry of lignocellulosic biomass isolated downstream of the discharge device of the present invention with (right hand side of curve) and without (left hand side of curve) agitation of the content of the device.

The dry matter and the amount of suspended solids was analysed according to (Weiss, Stickel et al. 2009, see ref. 5). The analysis results relating to measurements of the xylan content of the solid fraction is depicted in FIG. 3. FIG. 3 illustrates the xylan content measured eight times (represented by rhombic dots) at various intervals in the solid fraction in a run according to this example during a time span of 40 hours. In the first 20 hours, the hydrocyclone was operated with the agitation means in a switched-off mode. In the last 20 hours the hydrocyclone was operated with the agitation means in a switched-on mode.

FIG. 3 shows that in the first 20 hours run in which the agitation means provided no agitation, the xylan content of the solid fraction isolated averaged to approximately 5.0% (wt/wt).

However, in the last 20 hours of the run, in which the agitation means were switched on and did provide agitation to the aqueous slurry, the the xylan content of the solid fraction isolated averaged to approximately 9.0% (wt/wt).

This increase corresponds to an increase of 80% and is solely attributed to the effect of using the agitation means for agitation of the aqueous slurry present in the discharge device.

The increased content of xylan originates from a reduced decomposition of the hemicellulose and subsequent solubilisation. An increased content of xylan implies that more sugars are available for fermentation into ethanol downstream of the pretreatment steps, leading to an overall increased ethanol yield.

Figure 4:
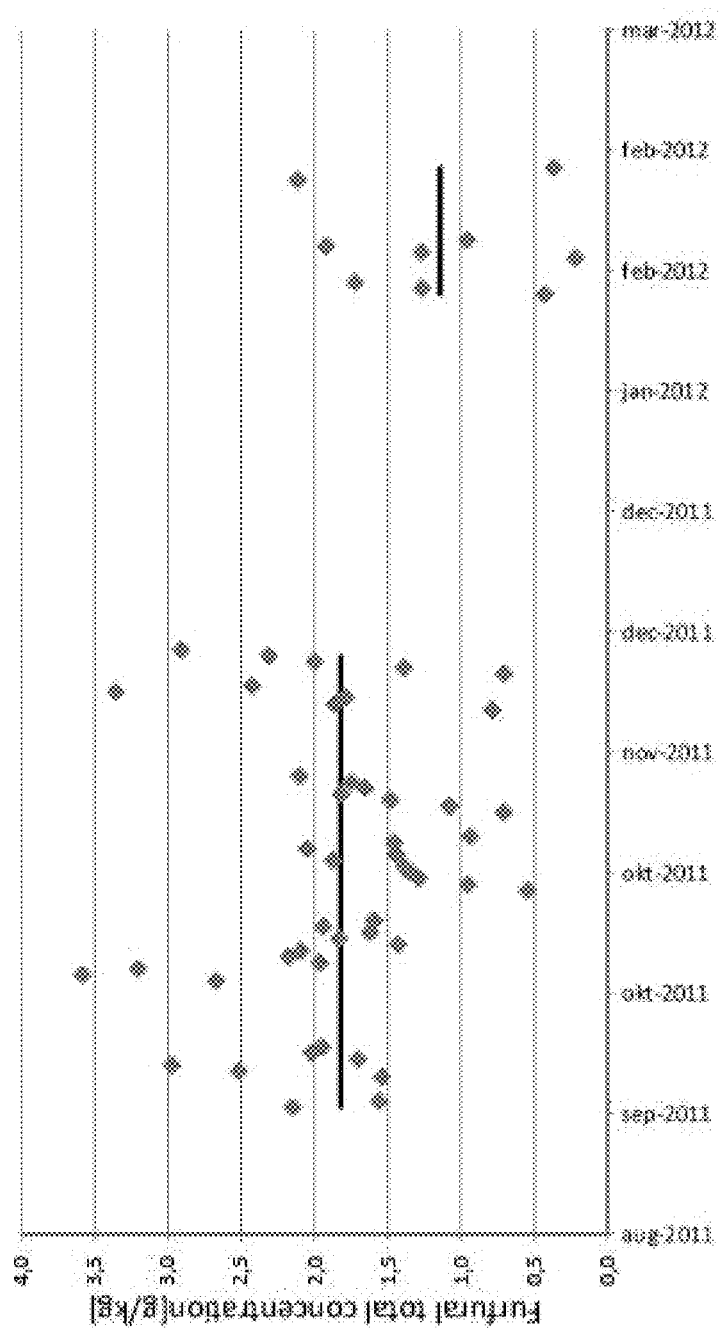
FIG. 4 illustrates furfural concentration in the liquid fraction of a slurry of lignocellulosic biomass isolated downstream of the device of the present invention with (right hand side of curve) and without (left hand side of curve) agitation of the content of the device.

FIG. 4 illustrates the analysis results relating to measurements of the furfural concentration of the liquid fraction of the slurry. FIG. 4 shows that the furfural concentration was measured a number of times (represented by rhombic dots) at various intervals during a period of time stretching over three months (September 2011 to December 2011) and later over a period of approximately one month (February 2012). In the first period, the discharge device was operated with the agitation means in a switched-off mode. In the last period the discharge device was operated with the agitation means in a switched-on mode.

FIG. 4 shows that in the first period in which the agitation means provided no agitation, the furfural concentration in the liquid fraction isolated averaged to approximately 1.8 g/kg (solid, bold line; left hand side of diagram).

However, in the last period, in which the agitation means were switched on and did provide agitation to the aqueous slurry, the furfural content of the liquid fraction isolated averaged to approximately 1.15 g/kg (solid, bold line; right hand side of diagram).

This reduction corresponds to a reduction of the furfural concentration of approximately 36% and is solely attributed to the effect of using the agitation means for agitation of the aqueous slurry present in the discharge device.

FIG. 4 shows that not only was the concentration of furfural reduced when having the agitation means switched on but additionally, the presence of extremely high concentrations of furfural in the liquid phase (as appearing in a few single samples) was eliminated.

A reduced concentration of furfural in the liquid phase implies that a reduced amount of furfural is carried along for further downstream processing by the solid material. As furfural act as a fermentation inhibitor, it will be beneficial to reduce the concentration of furfural in the liquid phase as much as possible, as this will lead to an overall increased ethanol yield.

FIG. 5a illustrates the temperature gradient encountered in the interior of the vessel of the hydrocyclone in a steady-state situation during the experiment of the example, wherein no agitation of the slurry of biomass was conducted. FIG. 5a shows the various heights relative to the bottom of the vessel of the hydrocyclone (i.e. 650 mm, 880 mm, 1110 mm, 1340 mm, 1570 mm, 1800 mm, 2030 mm and 2260 mm) at which positions or heights temperature sensors were located. In respect of each temperature sensor, a temperature is measured at the specific time of the experiment. These temperatures are presented in FIG. 5a and as can be seen they range from 187° C. at the highest arranged sensor of the vessel to 81° C. at the lowest arranged sensor. The boundary between the gas phase and the liquid phase is denoted by a dotted line which corresponds to a height of approximately 1500 mm.

FIG. 5a reveals that in the experiment in which no mechanical agitation of the biomass was employed, rather high temperatures were encountered by the biomass in the upper part of the vessel, i.e. in the gas phase as well as in the top layer of the liquid phase (the temperature in the top layer of the liquid phase was measured to be 152° C.

Accordingly, in the experiment in which no mechanical agitation of the biomass was employed, the biomass having been subjected to a hydrothermal pretreatment and entering the hydrocyclone will in the hydrocyclone encounter some additional "cooking" in the liquid phase of the vessel of the hydrocyclone before the biomass will become "temperature equalized" to a temperature below the boiling point of water. Such additional "cooking" accordingly adds to the "cooking" already encountered by the biomass in the hydrothermal pretreatment reactor and thus adds to the total severity of the treatment. This additional cooking result in the adverse effects of losing C5-saccharides from the biomass into the aqueous liquid and in the adverse effect of increasing the concentration of furfural in the aqueous liquid as evidenced by FIG. 3 and FIG. 4.

FIG. 5b illustrates the temperature gradient encountered in the interior of the vessel of the discharge device according to the present invention in a steady-state situation during the experiment of the example. FIG. 5b shows the various heights relative to the bottom of the vessel of the inventive discharge device (i.e. 650 mm, 880 mm, 1110 mm, 1340 mm, 1570 mm, 1800 mm, 2030 mm and 2260 mm) at which positions or heights temperature sensors were located. In respect of each temperature sensor, a temperature is measured at the specific time of the experiment. These temperatures are presented in FIG. 5b and as can be seen they range from 181° C. at the highest arranged sensor of the vessel to 81° C. at the lowest arranged sensor. The boundary between the gas phase and the liquid phase is denoted by a dotted line which corresponds to approximately a height of 1500 mm.

FIG. 5b reveals that in the experiment in which a mechanical agitation of the biomass was employed, the biomass, as soon as it had fallen through the upper gaseous phase, would encounter a significant cooler liquid phase as compared to the situation in respect of the example where no agitation was employed. As appearing in FIG. 5b, the liquid phase near its surface has a temperature of 91° C. or below.

It is generally agreed within the art of hydrothermal biomass pretreatment that a pretreatment temperature of biomass of below 100° C. virtually imparts no severity, and accordingly contributes to no loosening of the cellulose and no degradation of hemicellulose to the biomass being subjected to such temperature.

This means that compared to the situation in the example where no agitation of biomass was employed, the biomass being discharged into the discharge device will encounter no additional "cooking" in the vessel of the discharge device itself. Accordingly, with the mode of operation employed in this example, the degree severity degree subjected to the biomass can be much better controlled in that the severity imparted in a pretreatment reactor almost immediately stops once the biomass has entered the vessel of the discharge device.

The different temperature gradient situations associated with the situation in which agitation of biomass was employed or not employed, respectively, as illustrated in FIGS. 5a and 5b, at least partly explains the surprising findings as illustrated in FIGS. 3 and 4, viz. that providing a stirring of the biomass slurry having been loaded into the discharge vessel implies on the one hand a higher retaining of xylan species in the fibre fraction of the biomass, and on the other hand, a smaller degree of furfural formation and subsequent transfer of furfural into the liquid phase of the slurry.

The results of this example show that by providing a prior art device for discharging pretreated biomass from higher to lower pressure, with mechanical agitation means for equalising temperature differences at various heights in the aqueous phase of the content of that vessel during processing a lignocellulosic biomass it is possible to considerably reduce the loss of xylan content of the fibrous fraction of the biomass into the liquid phase.

Additionally, the experiments show that at the same time the content of furfural in the aqueous phase is significantly reduced. Furthermore, it has been found that the previously encountered problems associated with deposition of re-solidified lignin could be eliminated.

It should be understood that all features and achievements discussed above in relation to any one of the aspects of the device, the apparatus, the use and the method, respectively, of the present invention and any embodiments thereof apply equally well to the invention of the other of those aspects of the present invention.

REFERENCES

1. Y. Sun and J. Cheng, "Hydrolysis of lignocellulosic materials for ethanol production: a review", Bioresource Technology (2002) 83:1.
2. Felby, C., Klinke, H. B, Olsen, H. S, et al., "Ethanol from wheat straw cellulose by wetoxidation pretreatment and simultaneous saccharification and fermentation, APPLICATIONS OF ENZYMES TO LIGNOCELLU-LOSICS, Volume: 855, Pages: 157-174, Published: 2003.
3. Sluiter, A., et al., "Determination of Extractives in Biomass," US National Renewable Energy Laboratory (NREL), Laboratory Analytical Procedure (LAP) with issue date Jul. 17, 2005, NREL/TP-510-42619, revised January 2008.
4. Sluiter, A., et al., "Determination of Sugars, Byproducts, and Degradation Products in Liquid Fraction Process Samples," US National Renewable Energy Laboratory (NREL), Laboratory Analytical Procedure (LAP) with issue date Dec. 8, 2006, NREL/TP-510-42623, revised January 2008.
5. Weiss, N. D., et al., "A simplified Method for the Measurement of Insoluble Solids in Pretreated Biomass Slurries.", *Appl. Biochem. Biotechnol.* (2009), 975-987: 162(4).
6. Sluiter, A., et al., "Determination of Structural Carbohydrates and Lignin in Biomass," US National Renewable Energy Laboratory (NREL), Laboratory Analytical Procedure (LAP) with issue date Apr. 25, 2008, NREL/TP-510-42618, revised April 2008.

The invention claimed is:

1. A discharge device for discharging pretreated lignocellulosic biomass from higher to lower pressure, said discharge device in the orientation intended for use comprising:
    a vessel having an opening to a high pressure region at the top, and configured to be connected with a pressurized biomass pretreatment device;
    one or more inlet openings situated along the sides of the vessels through which water or liquid may be added;
    an orifice or valve at a lower part of said vessel, said orifice or valve being configured to eject pretreated biomass, optionally into a pipeline;
    wherein the discharge device comprises mechanical agitation means, said agitation means comprising an agitation element arranged in the interior of said vessel at a lower part of said vessel, and being configured to provide agitation of a content of said vessel, wherein said agitation means being adapted to withstand a pressure in the interior of a said vessel of 10 bar or more;
    characterized in that the discharge device comprises a loop conduit connecting one or more of said inlet openings to said orifice or valve at the lower part of the vessel, thereby forming a loop for recirculating of liquid or slurry; wherein said loop comprises means for separating pretreated biomass from liquid.

2. The discharge device according to claim 1, wherein said vessel is an upright oriented vessel.

3. The discharge device according to claim 1, wherein said vessel is cylindrical or conical.

4. The discharge device according to claim 1, wherein said mechanical agitation means comprises drive means and an agitation element, wherein said drive means providing mechanical movement to said agitation element via a connecting element, wherein said agitation element is arranged in the interior of said vessel, and wherein said drive means is arranged at the exterior of said vessel; wherein said agitation element and said drive means are being separated by a sealing.

5. The discharge device according to claim 4, wherein said sealing is adapted to withstand a pressure difference between the drive means and the agitation element of 10-52 bar.

6. The discharge device according to claim 4, wherein the power of said drive means in relation to the interior volume of said vessel is 1.5-8.0 kW/m$^3$.

7. The discharge device according to claim 4, wherein said connecting element is an axle.

8. The discharge device according to claim 1, wherein said agitation element is in the form of a rotor comprising a conical screw, a propeller, one or more blades, or a spiral.

9. The discharge device according to claim 1, wherein said vessel is having an internal volume of 500 L, or more.

10. The discharge device according to claim 1, wherein said agitation element being adapted to provide, during use of said discharge device, an equalization of temperatures within a specific vertical range of heights of an aqueous slurry present in said vessel in such a way that there exists a vertical range of heights, H of 40 cm or more in said aqueous slurry in respect of which the variation of temperatures, $\Delta T$ of said slurry is 30° C. or less.

11. The discharge device according to claim 10, wherein said vertical range of heights, H independently is 40-95 cm and/or wherein said variation of temperatures, $\Delta T$ of said slurry independently is 0-30° C.

12. The discharge device according to claim 1, wherein said discharge device furthermore comprises a conduit connecting one or more of the inlet openings to said orifice or valve at the lower part of said vessel, thereby forming a loop for recirculation of liquid or slurry; said loop for recirculating liquid or slurry optionally comprises means for separation of pretreated biomass from said liquid or slurry; said means for separation of pretreated biomass from said liquid optionally comprises a press.

13. The discharge device according to claim 12, wherein said press selected from the group consisting of: a single screw press, a twin screw press, a belt press, a drum filter, a centrifuge, and a decanter centrifuge.

14. The discharge device according to claim 1, wherein said vessel comprises one or more sensors for monitoring physical and/or chemical characteristics of the content of said vessel, said sensors being selected from the group comprising: temperature sensors, NIR-sensors, pH-sensors, electric conductivity sensors, microwave sensors for detecting dry matter content, one or more sensors for detecting height of level of slurry or liquid.

15. The discharge device according to claim 14 comprising a control unit for controlling operation of said device at least partly based on information representing readings from one or more of said sensors.

16. The discharge device of claim 14, wherein said sensors for detecting height of level of slurry or liquid are gamma sensors or differential pressure sensors.

17. The discharge device according to claim 1, wherein said opening to a high pressure region at the top of the vessel, and being configured to be connected with a pressurized biomass pretreatment device is adapted to allow biomass to enter said device by falling by gravity, vertically from said opening into said vessel.

18. The discharge device according to claim 1, wherein said opening to a high pressure region at the top of the vessel is having a cross-sectional area of 0.2-8 m$^2$.

19. The discharge device according to claim 1, wherein said vessel in use is adapted to allow liquid, solids and steam to exit the vessel by the same exit route(s).

20. The apparatus comprising a discharge device according to claim 1, in combination with a hydrothermal pretreatment reactor;
   wherein said hydrothermal pretreatment reactor comprising a cylinder being horizontally arranged and having an inlet for biomass at a first axial end and an outlet for biomass at a second axial end, opposite to said first end;
   wherein said cylinder comprises in its interior a rotatable auger screw, said auger screw being configured for conveyance of biomass from said first axial end to said second axial end;
   wherein said cylinder furthermore comprises one or more inlets for steam and/or water;
   wherein said outlet for hydrothermally pretreated biomass at a second axial end of said cylinder being connected to said opening arranged at the top of the vessel of said discharge device.

21. The apparatus according to claim 20, wherein said apparatus comprises an array of consecutively arranged cylinders, each cylinder being essentially horizontally arranged and having an inlet for biomass at a first axial end and an outlet for biomass at a second axial end opposite to said first end;
   wherein each said cylinder comprises in its interior a rotatable auger screw, said auger screw being configured for conveyance of biomass from said first axial end to said second axial end of said cylinder;
   wherein in respect of each cylinder, the outlet at a second axial end of said cylinder is connected to said inlet at a first axial end of a subsequent cylinder by a connection element;
   wherein in respect of the last cylinder in the array of consecutively arranged cylinders, the outlet of said last cylinder is being connected to said opening arranged at the top of the vessel of said discharge device.

22. The apparatus according to claim 21, wherein said array of consecutively arranged cylinders comprises 2-7 cylinders.

23. The apparatus according to claim 21, wherein each cylinder being arranged on top of its successive cylinder;
   wherein each connection element, connecting a cylinder with its successive cylinder, being essentially vertically arranged, thereby allowing a free fall of biomass in its transition from one cylinder to its successive cylinder.

24. The discharge device of claim 1, wherein said biomass comprises lignocellulosic biomass.

25. The discharge device of claim 24, wherein said lignocellulosic biomass is soft lignocellulosic biomass.

* * * * *